United States Patent
Jung et al.

(10) Patent No.: US 11,673,122 B2
(45) Date of Patent: Jun. 13, 2023

(54) GAS SENSOR USING METAL OXIDE SEMICONDUCTING NANOFIBER SENSITIZED BY ALKALI OR ALKALINE EARTH METAL AND NOBLE METAL CATALYSTS, AND MANUFACTURING METHOD THEREOF

(71) Applicants: SAMSUNG ELECTRONICS CO., LTD., Suwon-si (KR); KOREA ADVANCED INSTITUTE OF SCIENCE AND TECHNOLOGY, Daejeon (KR)

(72) Inventors: Won Jong Jung, Seoul (KR); Il Doo Kim, Daejeon (KR); Kak Namkoong, Seoul (KR); Dong Ha Kim, Daejeon (KR); Yeol Ho Lee, Anyang-si (KR); Joon Hyung Lee, Seongnam-si (KR); Ki Young Chang, Seoul (KR); Ji Soo Jang, Daejeon (KR); Ha Min Shin, Daejeon (KR); Yoon Hwa Kim, Daejeon (KR)

(73) Assignees: SAMSUNG ELECTRONICS CO., LTD., Suwon-si (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 67 days.

(21) Appl. No.: 17/321,689

(22) Filed: May 17, 2021

(65) Prior Publication Data
US 2022/0023838 A1    Jan. 27, 2022

(30) Foreign Application Priority Data
Jul. 27, 2020    (KR) .......................... 10-2020-0093283

(51) Int. Cl.
*B01J 23/42*    (2006.01)
*G01N 33/497*    (2006.01)
(Continued)

(52) U.S. Cl.
CPC ............... *B01J 23/42* (2013.01); *B01J 23/30* (2013.01); *B01J 35/006* (2013.01);
(Continued)

(58) Field of Classification Search
CPC ........ B01J 23/42; B01J 23/30; B01J 35/0013; B01J 35/006; B01J 35/06; B01J 35/1066;
(Continued)

(56) References Cited

U.S. PATENT DOCUMENTS 5,942,676 A    8/1999    Potthast et al.
7,476,376 B2   1/2009    Hong et al.
(Continued)

FOREIGN PATENT DOCUMENTS

KR    10-1349293 B1    1/2014
KR    101792438 B1 * 10/2017 ............. C01G 19/02
(Continued)

OTHER PUBLICATIONS

Sang-Joon Kim et al., "Mesoporous WO3 Nanofibers with Protein-Templated Nanoscale Catalysts for Detection of Trace Biomarkers in Exhaled Breath", ACS Nano, 2016, 9 pages total.
(Continued)

*Primary Examiner* — Patricia L. Hailey
(74) *Attorney, Agent, or Firm* — Sughrue Mion, PLLC

(57) ABSTRACT

A member for a metal oxide nanofiber based gas sensor can include a metal nanoparticle catalyst and can be formed to be functionalized by binding the metal nanoparticle catalyst and an alkali or alkaline earth metal through electrospinning and heat treatment processes. The member can detect a trace amount of a gas with high selectivity and ultra-high sensi-
(Continued)

tivity by uniformly binding the alkali or alkaline earth metal and the metal nanoparticle catalyst through electrospinning and high-temperature heat treatment.

20 Claims, 14 Drawing Sheets

(51) Int. Cl.
*B01J 23/30* (2006.01)
*B01J 35/00* (2006.01)
*B01J 35/06* (2006.01)
*G01N 27/12* (2006.01)
*B01J 35/10* (2006.01)
*B01J 37/00* (2006.01)
*B01J 37/04* (2006.01)
*B01J 37/34* (2006.01)

(52) U.S. Cl.
CPC .......... *B01J 35/0013* (2013.01); *B01J 35/06* (2013.01); *B01J 35/1066* (2013.01); *B01J 35/1071* (2013.01); *B01J 35/1076* (2013.01); *B01J 37/0018* (2013.01); *B01J 37/04* (2013.01); *B01J 37/342* (2013.01); *G01N 27/127* (2013.01); *G01N 33/497* (2013.01)

(58) Field of Classification Search
CPC  B01J 35/1071; B01J 35/1076; B01J 37/0018; B01J 37/04; B01J 37/342; G01N 27/127; G01N 33/497
USPC ........... 502/5, 306, 324, 328, 340, 343, 355; 977/811, 813
See application file for complete search history.

(56) References Cited

U.S. PATENT DOCUMENTS

| | | | |
|---|---|---|---|
| 8,535,632 | B2 | 9/2013 | Chase et al. |
| 9,304,102 | B2 | 4/2016 | Day et al. |
| 10,274,467 | B2 | 4/2019 | Kim et al. |
| 2011/0052467 | A1* | 3/2011 | Chase .................... B01J 23/464 502/332 |
| 2012/0041246 | A1 | 2/2012 | Scher et al. |
| 2012/0161796 | A1 | 6/2012 | Smith et al. |
| 2012/0201760 | A1* | 8/2012 | Tromsdorf ........... A61K 49/186 424/490 |
| 2019/0154645 | A1 | 5/2019 | Kim et al. |
| 2019/0169043 | A1 | 6/2019 | Nikolla et al. |

FOREIGN PATENT DOCUMENTS

| | | |
|---|---|---|
| KR | 10-1837287 B1 | 3/2018 |
| KR | 10-1893267 B1 | 8/2018 |
| KR | 10-1980442 B1 | 8/2019 |

OTHER PUBLICATIONS

Dong-Ha Kim et al., "Bioinspired Cocatalysts Decorated WO3 Nanotube Toward Unparalleled Hydrogen Sulfide Chemiresistor", ACS Sensors, 3, May 15, 2018, p. 1164-1173, 10 pages total.

Communication dated Nov. 26, 2021, issued by the European Patent Office in European Application No. 21180044.6.

Chengjun Dong et al., "A review on WO3 based gas sensors: Morphology control and enhanced sensing properties", Elsevier, Journal of Alloys an Compounds, Nov. 27, 2019, vol. 820, pp. 1-24 (24 pages total).

* cited by examiner

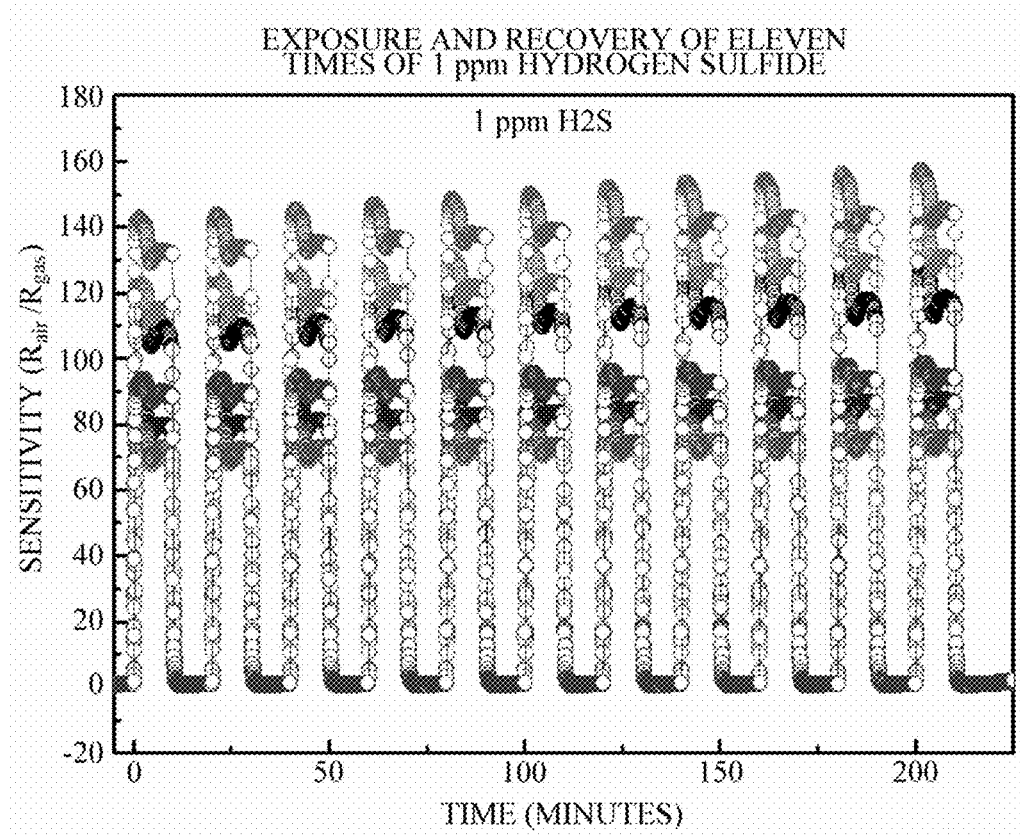

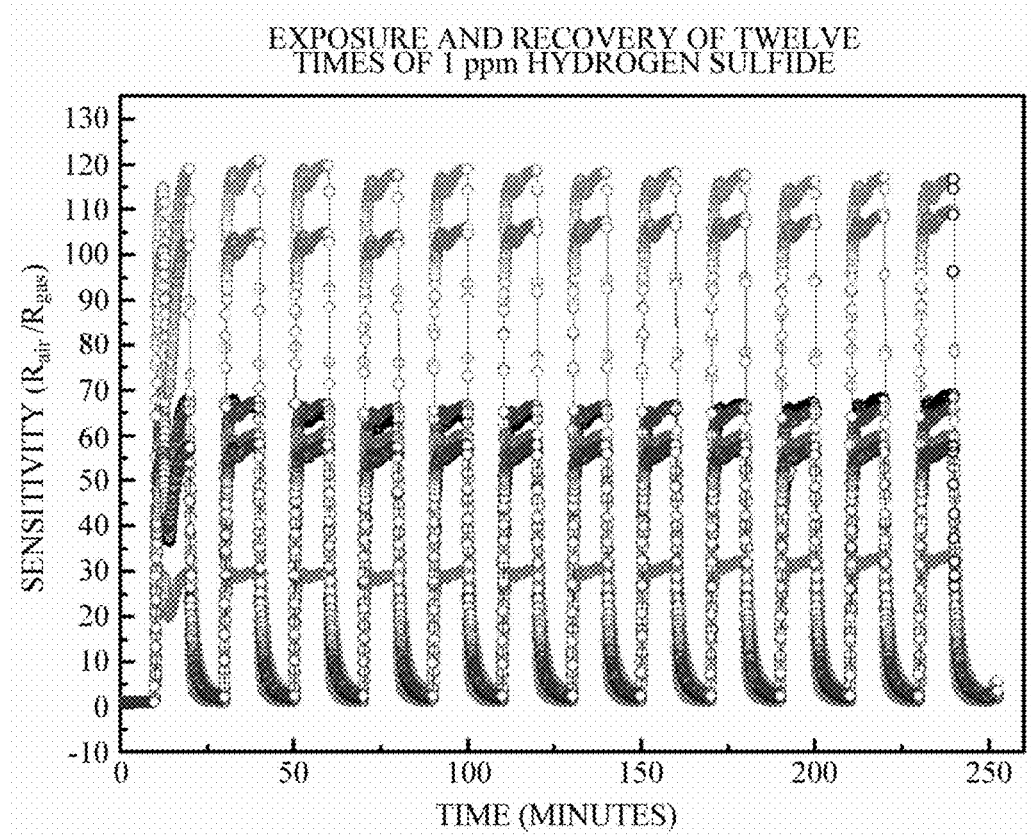

GAS SENSOR USING METAL OXIDE SEMICONDUCTING NANOFIBER SENSITIZED BY ALKALI OR ALKALINE EARTH METAL AND NOBLE METAL CATALYSTS, AND MANUFACTURING METHOD THEREOF

CROSS-REFERENCE TO RELATED APPLICATION(S)

This application claims priority from Korean Patent Application No. 10-2020-0093283, filed on Jul. 27, 2020, in the Korean Intellectual Property Office, the disclosure of which is incorporated herein by reference in its entirety.

BACKGROUND

1. Field

The following description relates to a member for a metal oxide nanofiber based gas sensor and a manufacturing method thereof.

2. Description of Related Art

Metal oxide semiconductor based gas sensors use a phenomenon which causes a variation in electrical resistance value due to a surface reaction in which a specific target gas molecule is adsorbed and desorbed on a surface of a metal oxide (a surface adsorption-desorption reaction). The performance of the gas sensor may be expressed as a resistance ratio ($R_{air}/R_{gas}$) of resistance in air and resistance when the sensor is exposed to a specific target gas, and high performance of the gas sensor may be exhibited when the resistance ratio $R_{air}/R_{gas}$ becomes large. Since a method of using the gas sensor is simple and miniaturization of the gas sensor is easy, there is an advantage in that it is possible to construct a sensor array system at a relatively low price, increase portability, and perform real-time measurement. Therefore, resistance change type metal oxide semiconductor based gas sensors have been used in various applications such as detection of harmful gases or detection of a biomarker gas in exhalation of a human body to diagnose a disease in an early stage. During a metabolic process, the biomarker gas is produced in a trace amount at a level in a range of ppb to ppm to be discharged through exhalation. Typically, the biomarker gas includes hydrogen sulfide ($H_2S$) gas, acetone ($CH_3COCH_3$) gas, and toluene ($C_6H_5CH_3$), and these gases are closely related to bad breath, diabetes, and lung cancer. In order to detect the trace amount of the biomarker gas, sensor performance having high sensitivity, high selectivity, and a high-speed response is required. However, the conventional metal oxide semiconductor gas sensor has a disadvantage in that a response time and a recovery time are long, ranging from several tens of seconds to several minutes or more, a selective reaction characteristic with a specific gas is low, and performance of a limit of detection is degraded. Thus, the development of a sensing material for a gas sensor which overcomes the above problems and is capable of reliably detecting an extreme trace amount of a gas with ultra-high sensitivity and high selectivity is desired.

In order to manufacture a metal oxide semiconductor based gas sensor having ultra-high sensitivity detection performance, it is necessary to synthesize various nanostructure-based detection materials. Thus, various structures such as nanoparticles, nanosheets, nanowires, and nanofibers have been developed, employed, and studied as sensor materials. Since each of the nanostructures has a large specific surface area to react with a gas over a large area, there is an advantage of allowing a gas detection characteristic to be improved and inducing diffusion of a gas into the nanostructure and a surface reaction of the gas with the nanostructure through a porous structure so that an ultra-high-speed reaction is possible. In particular, when the nanoparticles or the nanosheets are manufactured in the form of a film, there is a problem in that pores are clogged due to phenomena of agglomeration and restacking with each other so that deactivated reaction points (dead reaction sites), which are not involved in a reaction of detection materials which are present in a lower portion, are increased. On the other hand, since a one-dimensional metal oxide semiconductor nanofiber structure has a structure which is very advantageous in allowing a gas to be easily diffused through large pores which are present between nanofibers, the one-dimensional metal oxide semiconductor nanofiber structure is an ideal structure having excellent gas reactivity.

In order to improve sensitivity and selectivity characteristics of the metal oxide semiconductor based gas sensor, studies on binding a catalyst are being actively conducted. A catalyst can be used to provide chemical and electronic sensitization effects. For example, chemical sensitization binds precious metal catalysts such as platinum (Pt) and gold (Au) to increase concentrations of oxygen adsorption species ($O^-$, $O^{2-}$, and $O_2^-$) involved in chemical reactions on a surface of the metal oxide, while electronic sensitization based on a change in oxidation number (PdO or $Ag_2O$) can be achieved using palladium (Pd) and silver (Ag). In particular, it is very important to manufacture catalysts as small as several nanometers (nm) and uniformly bind the catalysts over a detection material. However, in the case of a polyol process which is commonly used, there is a disadvantage in that a metal catalyst is relatively large in a range of 3 nm to 10 nm or more and the metal catalysts are oxidized or are easily agglomerated with each other during high-temperature heat treatment so that a catalyst characteristic may be degraded.

SUMMARY

One or more example embodiments provide a member for a metal oxide nanofiber based gas sensor and a manufacturing method thereof.

According to an aspect of an example embodiment, there is provided a member for a gas sensor, the member including metal oxide nanofibers, wherein the metal oxide nanofibers include a metal nanoparticle catalyst and an alkali or alkaline earth metal bound to be functionalized between metal oxide nanoparticles through an electrospinning process followed by a heat treatment process.

A diameter of the metal oxide nanofiber may be in a range of 50 nm to 10 μm, and a length thereof may be in a range of 1 μm to 100 μm.

The metal oxide nanofiber may be in the form of a metal oxide in which at least one metal ion, which is selected from among $WO_3$, ZnO, $SnO_2$, $TiO_2$, $In_2O_3$, $Zn_2SnO_4$, and $MnO_2$, which are n-type semiconductors, or CuO, $Co_3O_4$, $Fe_2O_3$, $Fe_3O_4$, PdO, $LaCoO_3$, NiO, $NiCo_2O_4$, and $Ag_2O$, which are p-type semiconductors, may be oxidized.

The metal oxide nanofiber may have an open pore structure in a size range of 50 nm to 100 μm between the metal oxide nanofibers which are networked and interconnected and/or the metal oxide nanofiber itself may have an open pore formed therein.

The metal nanoparticle catalyst may be manufactured from an apoferritin protein template having a hollow structure having an inner diameter ranging from 7 nm to 8 nm in size.

The metal nanoparticle catalyst may be synthesized by injecting a metal salt into the apoferritin protein template and performing a reduction treatment through a reducing agent.

In this case, the metal salt may contain one or more among Pt, Pd, Rh, Ru, Ni, Co, Cr, Ir, Au, Ag, Zn, Mn, Ga, Ge, W, Sn, Sr, In, Pb, Ta, Sb, Sc, and Ti.

A size of the metal nanoparticle catalyst may be in a range of 1 nm to 5 nm.

The alkali or alkaline earth metal may include one or more among Na, K, Mg, Ca, Rb, Sr, Cs, and Ba.

The metal oxide nanofiber may include a second phase which is formed due to reaction of the alkali or alkaline earth metal with a metal oxide nanofiber matrix through a high temperature heat treatment.

The metal oxide nanofiber may include a plurality of heterointerfaces formed so that a second phase is formed due to reaction of the alkali or alkaline earth metal with a metal oxide nanofiber matrix and formed between the metal oxide nanofiber matrix, the second phase, and the metal nanoparticle catalyst.

In this case, for example, the alkali or alkaline earth metal may include Na, the metal oxide nanofiber matrix may include $WO_3$, and the plurality of heterointerfaces may include a $WO_3/Na_xW_yO$ heterointerface, a $WO_3$/metal catalyst interface, and a $Na_xW_yO_z$/metal catalyst interface as the Na and the $WO_3$ react to form a $Na_xW_yO_z$ phase.

According to an aspect of an example embodiment, there is provided a method of manufacturing metal oxide nanofibers, the method including synthesizing a nanoparticle catalyst inside an apoferritin protein template; preparing a spinning solution by stirring the apoferritin template containing the nanoparticle catalyst and an alkali or alkaline earth metal salt with a metal oxide precursor/polymer composite solution; electrospinning the spinning solution to synthesize metal oxide precursor/polymer composite nanofibers in which the nanoparticle catalyst and the alkali or alkaline earth metal salt are uniformly distributed; and synthesizing one-dimensional porous metal oxide nanofibers by performing heat treatment on the synthesized composite nanofibers.

In the synthesizing of the nanoparticle catalyst, a metal salt may be injected into inner pores of the apoferritin protein template, and reduction treatment may be performed using a reducing agent to synthesize the metal nanoparticle catalyst.

In the preparing of the spinning solution, a ratio by weight of the polymer to the nanoparticle catalyst may be in a range of 1:0.00001 to 1:0.1.

In the preparing of the spinning solution, a ratio by weight of the polymer to the alkali or alkaline earth metal salt may be in a range of 1:0.00001 to 1:0.1.

In the preparing of the spinning solution, stirring may be performed at a temperature ranging from 20 degrees Celsius to 40 degrees Celsius for four to twenty-four hours.

In the synthesizing of the metal oxide nanofibers, the nanoparticle catalyst and a second phase generated due to the alkali or alkaline earth metal salt may be uniformly distributed and bound through the heat treatment.

In the synthesizing of the metal oxide nanofibers, the heat treatment may be performed at a temperature ranging from 500 degrees Celsius to 800 degrees Celsius.

In the synthesizing of the metal oxide nanofibers, the apoferritin protein template and the polymer may be thermally decomposed and removed through the heat treatment, and the metal oxide precursor may be oxidized to form a one-dimensional metal oxide nanofiber structure.

BRIEF DESCRIPTION OF THE DRAWINGS

The above and/or other aspects, features, and advantages of certain example embodiments will be more apparent from the following description taken in conjunction with the accompanying drawings, in which:

FIGS. 9A and 9B are graphs showing stability of a gas sensor substrate which is manufactured according to an example embodiment.

DETAILED DESCRIPTION

Figure 1:
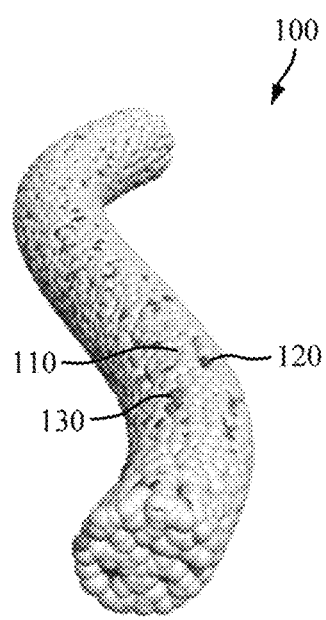
FIG. 1 is a schematic diagram illustrating a member for a one-dimensional metal oxide nanofiber based gas sensor, to which nanoparticle catalysts are uniformly bound, according to an example embodiment.

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

Throughout the accompanying drawings and the detailed description, unless otherwise described, the same drawing reference numerals will be understood to refer to the same elements, features, and structures. The relative size and depiction of these elements may be exaggerated for clarity, illustration, and convenience.

Hereinafter, various embodiments will be described with reference to the accompanying drawings. Various modifications may be flexibly applied to the embodiments, and thus various embodiments may be achieved. Hereinafter, specific embodiments will be described in detail with reference to the accompanying drawings. In describing the embodiments, when a detailed description of a known related art is determined to obscure the gist of the embodiments, detailed descriptions thereof will be omitted herein.

The terms first, second, and the like may be used to describe various components, but the components are not limited by these terms, and the terms may be used only to distinguish one component from another component.

Hereinafter, a member for a metal oxide nanofiber based gas sensor, a gas sensor, and a method of manufacturing the same, in which an alkali or alkaline earth metal group and precious metal nanoparticle catalysts through a protein template technique are functionalized in a complex manner, will be described in detail with reference to the accompanying drawings.

According to embodiments, a metal oxide nanofiber based gas sensor member in which a metal oxide precursor/polymer electrospinning solution, which contains alkali or alkaline earth metal salts as well as precious metal nanoparticle catalysts, is electrospun and heat-treated at a high temperature to compositely functionalize a precious metal catalyst and an alkali or alkaline earth metal will be disclosed herein. Here, a polymer solution in which the metal salts are dissolved may be defined as a metal oxide precursor/polymer and, after the heat treatment, the metal salts may be oxidized to form metal oxide nanofibers. In particular, during the high-temperature heat treatment, the alkali or alkaline earth metal may react with a metal oxide matrix to form metal oxide heterophases in a second phase. By controlling contents of the nanoparticle catalyst and the alkali or alkaline earth metal, it is possible to optimize detection performance. In addition, mass synthesis may be facilitated and reproducibility may be improved through electrospinning.

FIG. 1 is a schematic diagram illustrating a member for a one-dimensional metal oxide nanofiber based gas sensor, to which nanoparticle catalysts are uniformly bound, according to an example embodiment.

As shown in the drawing, one-dimensional metal oxide nanofibers 100 may be functionalized by binding metal oxide nanoparticles 110 serving as a matrix, metal nanoparticle catalysts 120, and metal oxide second phases 130 in which a phase change occurred due to addition of alkali or alkaline earth metal salts.

The metal nanoparticle catalysts 120 may be uniformly and evenly bound between individual grains of the metal oxide nanoparticles 110 which constitute polycrystalline metal oxide nanofibers by electrospinning a metal oxide precursor/polymer composite solution containing the alkali or alkaline earth metal salts and the metal nanoparticle catalysts 120 formed through an apoferritin protein template technique.

The metal nanoparticle catalysts 120 may be synthesized by injecting the metal salts into the apoferritin protein template and performing a reduction treatment using a reducing agent. A particle size of the metal nanoparticle catalyst 120 may be in a range of 1 nm to 5 nm. Here, the apoferritin protein template may have a hollow structure having a diameter ranging from 7 nm to 8 nm therein. The metal salt injected into pores of the apoferritin protein template is not particularly limited as long as it is a metal which can be present in an ionic state. For example, the metal salt may include one or more of Pt, Pd, Rh, Ru, Ni, Co, Cr, Ir, Au, Ag, Zn, Mn, Ga, Ge, W, Sn, Sr, In, Pb, Ta, Sb, Sc, or Ti. In addition, the reducing agent may include sodium borohydride ($NaBH_4$), oxalic acid ($C_2H_2O_4$), formic acid (HCOOH), or the like, and the present disclosure is not particularly limited thereto as long as it can form a metal nanoparticle catalyst by reducing a metal salt.

The composite nanofibers synthesized through electrospinning are heat-treated at a high-temperature so that at least a portion of the alkali or alkaline earth metal may react with the metal oxide matrix to form the second phase 130. Here, the alkali or alkaline earth metal includes, for example, Na, K, Ca, Mg, Rb, Sr, Cs, Ba, or the like, but the present disclosure is not limited thereto. Thus, the metal nanoparticle catalysts 120 are bound, and simultaneously, a plurality of heterointerface junctions may be formed between the metal oxides of the second phases 130 due to a phase change in metal oxide matrix-alkali or alkaline earth metal. For example, when the metal oxide matrix is $WO_3$ and the alkali or alkaline earth metal is Na, a second phase of $Na_xW_yO_z$ (e.g., $Na_2W_2O_{13}$) may be formed due to high-temperature heat treatment. Consequently, a $WO_3/Na_xW_yO_z$ heterointerface, a $WO_3$/metal catalyst interface, and a $Na_xW_yO_z$/metal catalyst interface may be simultaneously present in the metal oxide nanofibers.

The composite nanofibers synthesized through electrospinning are heat-treated at a high temperature so that metal oxide precursors and the alkali or alkaline earth metal salts are oxidized to form oxides, and simultaneously, the apoferritin template and the polymer are thermally decomposed and removed. Thus, the metal nanoparticle catalysts 120 and the second phases 130 due to the alkali or alkaline earth metal are uniformly distributed and bound so that the functionalized one-dimensional metal oxide nanofibers 100 are synthesized. In this case, when reacted with a specific gas, the second phase may give selectivity through an additional phase change and an electronic sensitization effect and may be restored to the original phase through a recovery process.

Figure 11:
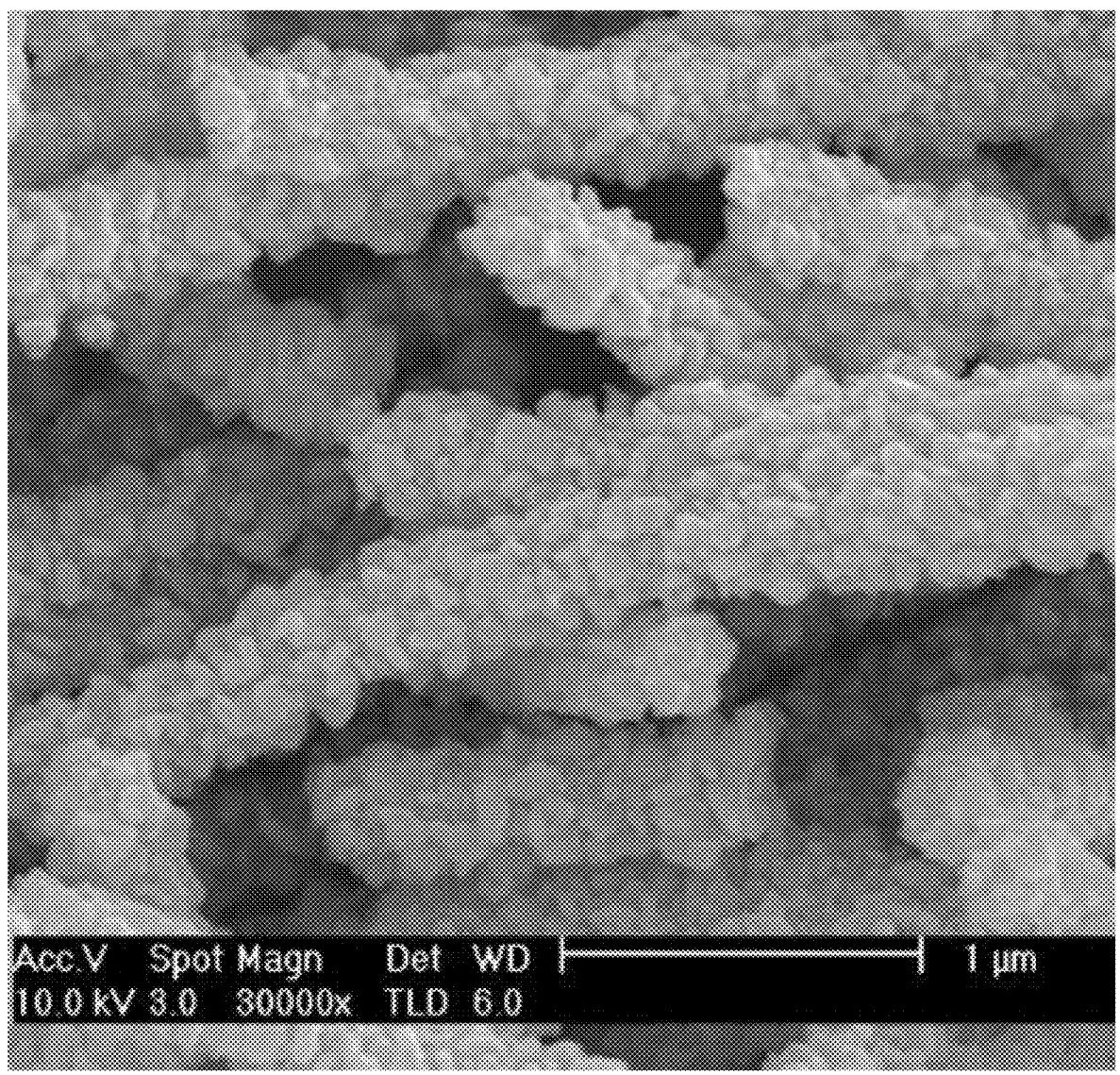
FIG. 11 is a SEM photograph showing a plurality of the metal oxide nanofibers of the present disclosure which are networked and interconnected.

A diameter of the metal oxide nanofiber 100 may be in a range of 50 nm to 10 μm, and a length of the metal oxide nanofiber 100 may be in a range of 1 μm to 100 μm. Here, the metal oxide nanofibers 100 may not be limited by n-type and p-type semiconductor properties and may be in the form of one or more metal oxides selected from among $WO_3$, ZnO, $SnO_2$, $TiO_2$, $In_2O_3$, and $Zn_2SnO_4$ which are n-type semiconductors, or CuO, $Co_3O_4$, $Fe_2O_3$, $Fe_3O_4$, PdO, $LaCoO_3$, NiO, $NiCo_2O_4$, $Ag_2O$ which are p-type semiconductors. The metal oxide nanofiber 100 may have an open pore structure in a size range of 50 nm to 100 μm, corresponding to an average pore diameter, between the metal oxide nanofibers which are networked and interconnected. Herein, the phrase "which are networked and interconnected" means a plurality of metal oxide nanofibers being networked and interconnected. This is shown, for example, in FIG. 11. The metal oxide nanofiber 100 itself may also have an open pore formed therein.

As described above, it is possible to selectively detect a biomarker gas discharged from exhalation of a person, which simultaneously exhibits catalyst effects of chemical and electronic sensitization, detect a disease of the human body in an early stage, and monitor harmful environmental gases in real time using a member for the one-dimensional metal oxide nanofiber based gas sensor which is functionalized such that the metal nanoparticle catalysts 120 and the second phases 130 formed due to the phase change of the alkali or alkaline earth metal salt through high temperature heat treatment are uniformly distributed and bonded.

Figure 2:
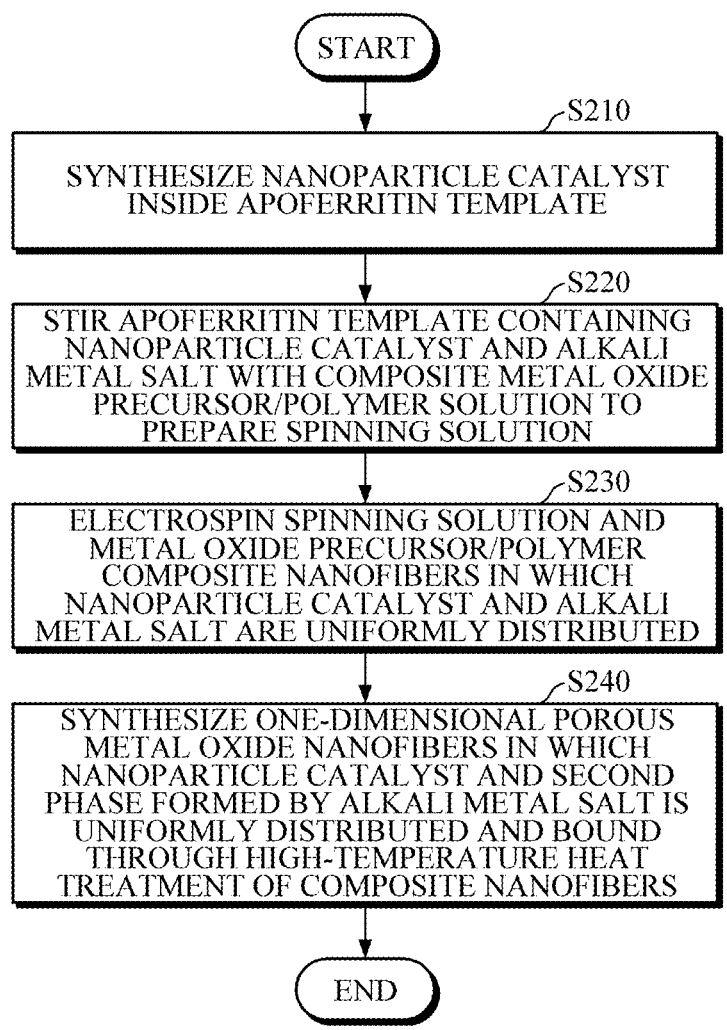
FIG. 2 is a flowchart illustrating a method of manufacturing a member for a one-dimensional metal oxide nanofiber based gas sensor including nanoparticle catalysts according to an example embodiment.

FIG. 2 is a flowchart illustrating a method of manufacturing a member for a gas sensor using a porous metal oxide nanofiber structure in which a nanoparticle catalyst formed of a sacrificial protein layer is functionalized and heterophases are obtained due to alkali or alkaline earth metal doping according to an example embodiment.

First, it is possible to synthesize the metal nanoparticle catalyst using the apoferritin template (S210). The apoferritin template may be used by removing iron ions in ferritin which is obtained without regard to an extraction target and an extraction site. A solution state in an acidic atmosphere in a range of pH 2 to pH 3 or a basic atmosphere in a range of pH 7.5 to pH 8.5 is suitable for the metal salt to diffuse into the apoferritin template through a hydrophilic channel of the apoferritin template. In order to allow the metal salt to sufficiently and uniformly diffuse into the apoferritin template, apoferritin is put in a solution, in which the metal salt is dissolved for a sufficient time in a range of one hour to twenty four hours, and stirred.

A concentration of the saline solution containing the apoferritin template may be in a range of 0.1 mg/ml to 200 mg/ml. In addition, when a metal salt solution is prepared, a commercially available solvent such as ethanol, deionized water, chloroform, N,N'-dimethylformamide, and N-methylpyrrolidone may be employed as a solvent and there is no limitation in using a specific solvent as long as a solvent can easily dissolve the metal salt. Here, types of metal salts diffusing into inner pores of the apoferritin include Pt, Pd, Rh, Ru, Ni, Co, Cr, Ir, Au, Ag, Zn, Mn, Ga, Ge, W, Sn, Sr, In, Pb, Ta, Sb, Sc, Ti, and the like, and a metal is not limited to a specific metal as long as it can be present in an ionic state.

Alternatively, the metal nanoparticle catalyst may be synthesized by reducing the metal salt diffusing in the inner pores of the apoferritin template into a metal using a reducing agent. In addition, the reducing agent may include $NaBH_4$, $C_2H_2O_4$, HCOOH, or the like, and there is no limitation in a type of the reducing agent as long as the reducing agent can form a metal nanoparticle catalyst by reducing a metal salt. In order to selectively extract the metal nanoparticle catalyst reduced with a reducing agent and the apoferritin template surrounding the metal nanoparticle catalyst, centrifugation can be performed at a rotational speed of about 1,000 to 100,000 rpm, such as, for example, about 12,000 rpm, and the extracted metal nanoparticles and the apoferritin template surrounding the extracted metal nanoparticles are re-distributed in deionized water.

Then, the apoferritin template containing the synthesized metal nanoparticle catalyst and the alkali or alkaline earth metal salt are added to the composite metal oxide precursor/polymer solution, and the nanoparticle catalyst and the alkali or alkaline earth metal salt are stirred so as to be uniformly distributed such that a mixed spinning solution is prepared (S220). In this case, when the spinning solution is prepared, a commercially available solvent such as deionized water, N,N'-dimethylformamide, N,N'-dimethylacetamide, ethanol, or the like may be employed as a solvent and there is no limitation in types of solvents as long as the solvent can simultaneously dissolve a metal oxide precursor (metal salt) and a polymer. In addition, types of polymers are not limited as long as the polymer contained in the spinning solution can be thermally decomposed and removed during high-temperature heat treatment. Further, the metal oxide precursor should be easily dissolved in an electrospinning solvent, and when a gas is introduced during the high temperature heat treatment, a precursor is not limited to a specific metal salt as long as the precursor containing a metal salt can form semiconductor-type metal oxide nanofibers in which resistance and electrical conductivity are varied through a surface adsorption/desorption reaction with a gas.

In this case, a weight ratio of the metal oxide precursor to the polymer in the electrospinning solution may be about 1:1 to 1:2, but the present disclosure is not particularly limited thereto. In addition, a weight ratio of the polymer to the nanoparticle catalyst contained in the apoferritin template may be about 1:0.00001 to 1:0.1. In addition, a weight ratio of the polymer to the alkali or alkaline earth metal salt may also be about 1:0.00001 to 1:0.1. In addition, an amount of the solvent in the electrospinning solution may be appropriately adjusted such that the solution does not have difficulty in electrospinning due to an excessive increase or decrease in viscosity. In the case of the nanoparticles contained in the apoferritin template, a metal salt may be selected according to selectivity of a gas to be detected. In addition, these conditions are appropriately adjusted so that it is possible to manufacture a member for a highly sensitive and highly selective gas sensor having various gas detection characteristics.

In the preparation of the electrospinning solution (S220), after the apoferritin template and the nanoparticle catalyst contained therein are uniformly distributed in the solvent, the alkali or alkaline earth metal salt, the metal oxide precursors, and the polymer for providing viscosity are added in an appropriate ratio and dissolved. In this case, stirring is performed until all the additives are dissolved, and a condition of the stirring may be sufficiently satisfied at a temperature ranging from 20 degrees Celsius to 100 degrees Celsius for four to twenty-four hours. Through such a process, it is possible to prepare the mixed electrospinning solution in which the apoferritin template containing the nanoparticle catalyst and the alkali or alkaline earth metal salt are uniformly distributed together with the metal oxide precursors and the polymer.

Then, composite nanofibers in the form in which the apoferritin template containing the nanoparticle catalyst and the alkali or alkaline earth metal salt are uniformly bound are synthesized by electrospinning the spinning solution prepared in operation S220 (S230). The electrospinning may be performed by filling a syringe with the electrospinning solution and pushing the electrospinning solution in the syringe at a constant speed using a syringe pump to discharge the electrospinning solution. In this case, a discharge rate may be adjusted within a range of 0.01 ml/min to 1 ml/min. A high voltage ranging from 1 kV to 50 kV is applied between the syringe containing the electrospinning solution and a conductive substrate, and the electrospinning solution is discharged through a nozzle to be spun in the form of nanofibers and collected on the conductive substrate.

Finally, the composite nanofibers which are synthesized in operation S230 are heat-treated at a high temperature to synthesize one-dimensional porous metal oxide nanofibers in which the nanoparticle catalysts and the second phases formed by the alkali or alkaline earth metal salt is uniformly distributed and bound (S240). During the high-temperature heat treatment, the metal oxide precursors and the alkali or alkaline earth metal salt are oxidized to form the metal oxide and, simultaneously, the apoferritin template and the polymer are thermally decomposed and removed. Consequently, it is possible to manufacture the one-dimensional metal oxide nanofibers functionalized by which the nanoparticle catalysts and the second phases formed by the alkali or alkaline earth metal are uniformly distributed and bound. In this case, the high-temperature heat treatment may be performed at a temperature ranging from 500 degrees Celsius to 800 degrees Celsius, the polymer and the apoferritin template are oxidized and removed, and the metal oxide precursors are oxidized and crystallized through a nucleus growth and a grain growth to form a one-dimensional metal oxide nanofiber structure.

Figure 3:
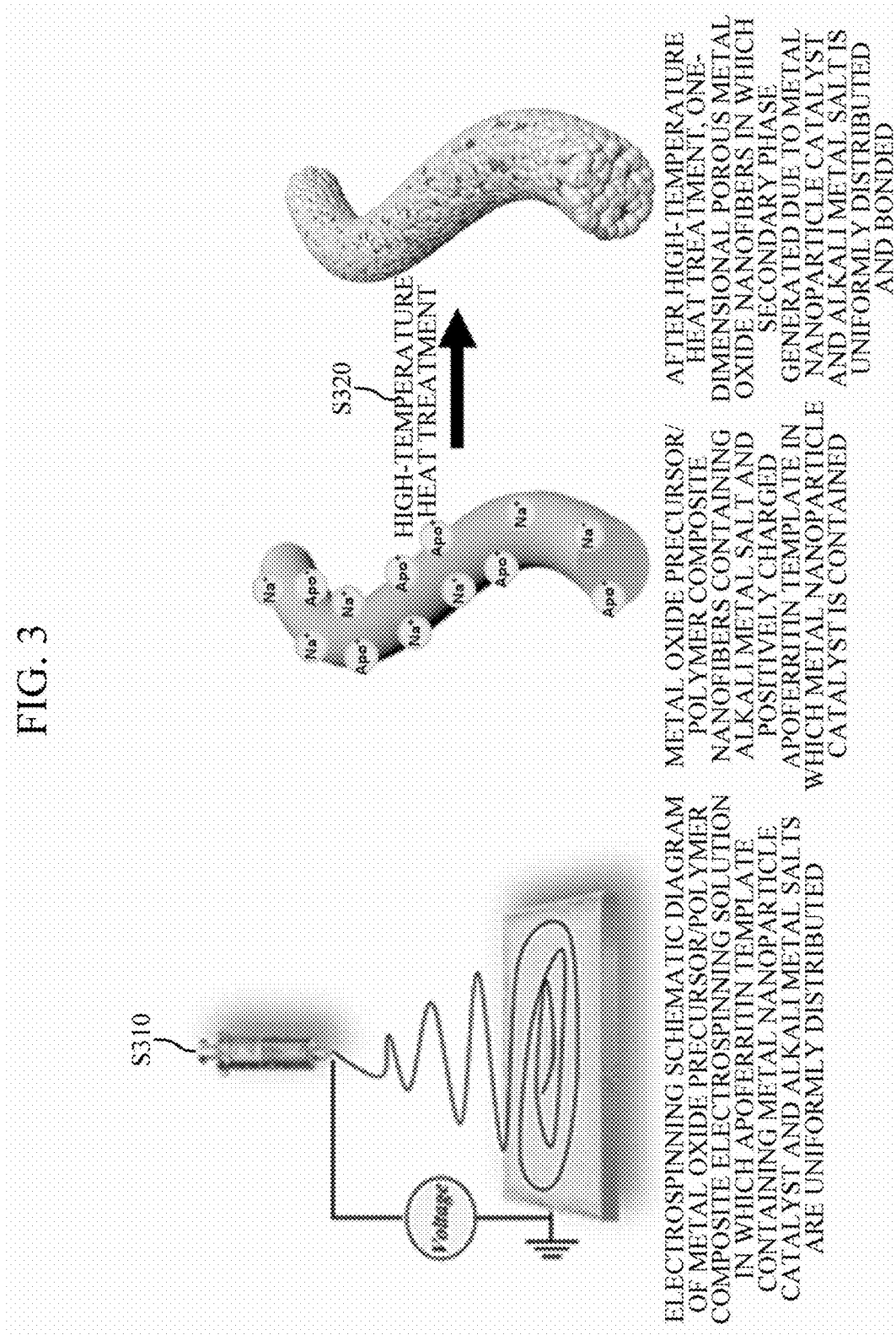
FIG. 3 is a diagram illustrating a manufacturing process of a one-dimensional metal oxide nanofiber structure to which nanoparticle catalysts are uniformly bound using an electrospinning method according to an example embodiment.

FIG. 3 schematically illustrates a manufacturing process sequence according to a method of manufacturing a member for a gas sensor using the one-dimensional metal oxide nanofibers in which the metal nanoparticle catalysts and the second phases based on the alkali or alkaline earth metal salt are uniformly bound and distributed using an electrospinning method according to an example embodiment.

Operation S310, which is a first procedure, is a schematic diagram illustrating a process of electrospinning a metal oxide precursor/polymer electrospinning solution, in which the alkali or alkaline earth metal salt and the apoferritin template containing the nanoparticle catalyst are uniformly distributed, using electrospinning.

Operation S320, which is a second procedure, is a schematic diagram illustrating a process of performing the high-temperature heat treatment on nanofibers, which are collected on the conductive substrate through the electrospinning in operation S310, to thermally decompose and remove a polymer matrix and the apoferritin template which are contained in the nanofibers, uniformly binding the metal nanoparticle catalyst, and synthesizing a member for a gas sensor using a plurality of one-dimensional metal oxide nanofibers in which the second phases are uniformly distributed due to alkali or alkaline earth metal doping.

According to the embodiments, electrospinning and the method of manufacturing a member for a gas sensor using one-dimensional metal oxide nanofibers, in which the precious metal nanoparticle catalyst is functionalized through the apoferritin template technique and the second phases are uniformly distributed and bound using the alkali or alkaline earth metal salt, simultaneously exhibit chemical and electronic sensitization catalyst effects through effective composite functionalization of the second phase formed by doping of the alkali or alkaline earth metal together with the metal nanoparticle catalyst which is very uniformly distributed in a small size through the apoferritin template technique so that sensitivity and selectivity may be improved as compared with those of the conventional gas sensor.

Hereinafter, Examples and Comparative Examples will be described in detail. The Examples and the Comparative Examples, which will be described below, are merely to aid understanding of the present disclosure and are not limited to the following examples.

Example 1: Preparation of Pt Nanoparticle Catalyst Using Apoferritin Template

An apoferritin template is a protein template having an outer diameter ranging from about 11 nm to 12 nm and an inner diameter ranging from 7 nm to 8 nm. The following procedure is performed so as to synthesize a Pt nanoparticle catalyst having a size range of about 1 nm to 5 nm in apoferritin using the apoferritin template.

In order to allow a metal salt to be contained in the apoferritin, an apoferritin solution (Sigma Aldrich) which is distributed in 0.15 M NaCl aqueous solution at a concentration of 35 mg/ml was prepared. A NaOH basic aqueous solution was added to the apoferritin solution to adjust a pH to about pH 8.5 to form a hydrophilic tunnel of the apoferritin template, thereby satisfying an optimum condition for the metal salt from the outside to easily flow into the inside. $H_2PtCl_6$ and $H_2O$ were used for precursors of Pt metal ions, and about 10 mg of $H_2PtCl_6H_2O$ was dissolved in 1 g of deionized water to be prepared in the form of an aqueous solution. Here, the metal salt precursor aqueous solution was dropped and added to the apoferritin template solution of which the pH was adjusted to around pH 8.5 using a pipette and stirred at room temperature. In this case, a suitable stirring speed was 100 rpm, and the stirring was maintained for about one hour. After the stirring was sufficiently performed, a $NaBH_4$ reducing agent was synthesized in a state of an aqueous solution at a concentration of 40 mM, and then 0.5 ml $NaBH_4$ reducing agent was added to the apoferritin solution so that the metal salt present in the apoferritin was reduced to metal nanoparticles. In this case, since an impurity may be present in the apoferritin solution containing the synthesized Pt nanoparticle catalyst, washing was performed using centrifugal separation and then the apoferritin template containing a pure Pt nanoparticle catalyst was extracted and distributed in deionized water.

Figure 4:
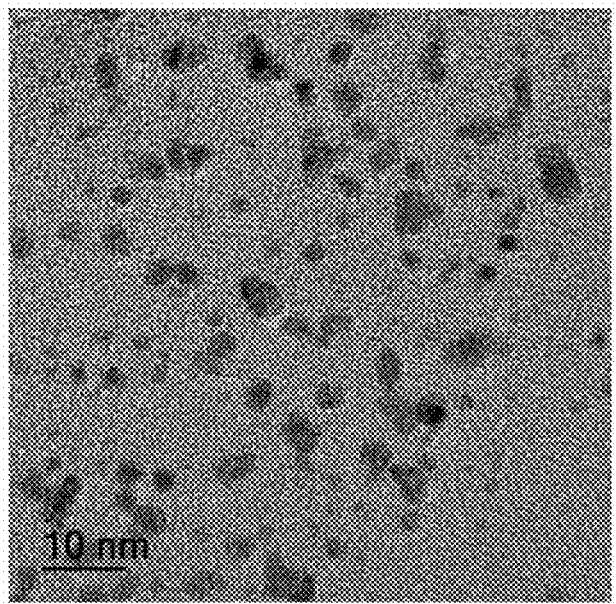
FIG. 4 is a transmission electron microscope (TEM) photograph showing bound platinum (Pt) nanoparticle catalysts inside an apoferritin template according to Example 1.

FIG. 4 is a transmission electron microscope (TEM) photograph showing the bound Pt nanoparticle catalysts inside the apoferritin template according to Example 1. It can be confirmed that the Pt nanoparticle catalysts were uniformly distributed in a uniform size through the TEM photograph.

Example 2: Manufacturing of One-Dimensional Tungsten Oxide (WO) Nanofiber Structure Doped with Pt Precious Metal Catalyst and Na Primarily, after 5 mg of NaCl was dissolved in 2 g of deionized water, ammonium tungsten metatungstate hydrate, which is 0.266 g of tungsten oxide precursors and 0.333 g of polyvinylpyrrolidone (PVP) polymer having a molecular weight of 1,300,000 g/mol, were additionally mixed. Then, 10 microliters of the Pt nanoparticle catalyst aqueous solution synthesized in Example 1 was mixed. The mixed solution was stirred at 500 rpm at room temperature for twelve hours to prepare a spinning solution. The prepared spinning solution was put in a syringe (Henke-Sass Wolf, 12 mL NORM-JECT®), the syringe was connected to a syringe pump, the electrospinning solution was pushed out at a discharge rate of 0.1 ml/min, and then electrospinning was performed by applying a voltage of 15 kV between a needle (25 gauge), which was used during spinning, and a current collector that collects the nanofibers. In this case, a stainless steel plate was used as the current collector, and a distance between the nozzle and the current collector was set to 20 cm. Thereafter, the polymer material was removed through an oxidation process, and the metal oxide precursor was oxidized to form tungsten oxide. In this case, a condition of the high-temperature heat treatment may be achieved by raising a temperature to 600° C. at a temperature increase rate of 5° C./min and then maintaining the temperature of 600° C. for one hour, and a temperature decrease rate may be kept constantly at 40° C./min.

Figure 5:
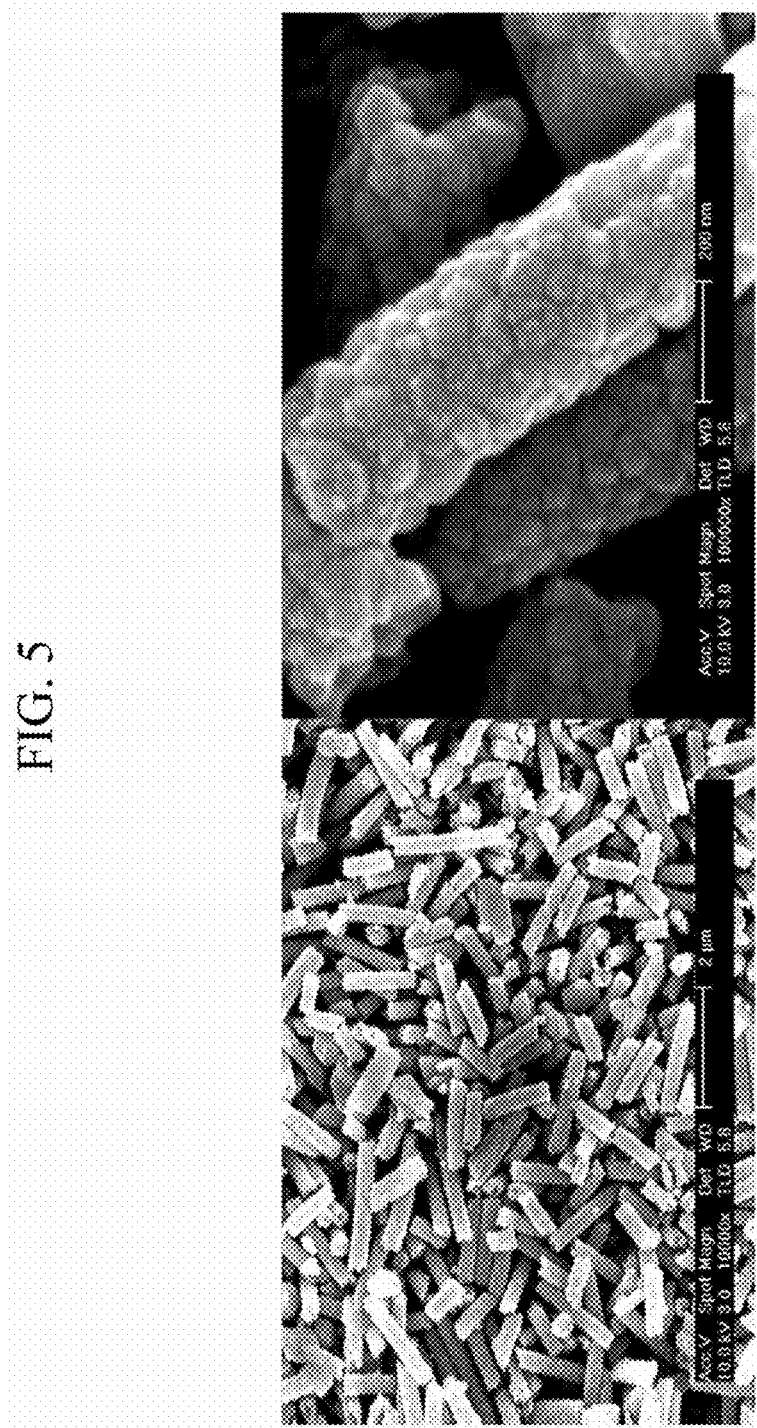
FIG. 5 shows scanning electron microscope (SEM) photographs showing one-dimensional tungsten oxide nanofibers doped with Pt nanoparticle catalysts and sodium (Na) through electrospinning and high-temperature heat treatment according to Example 2.

FIG. 5 illustrates scanning electron microscope (SEM) photographs showing the one-dimensional tungsten oxide nanofibers doped with Na and the Pt nanoparticle catalyst which is synthesized by performing high-temperature heat treatment on the composite fiber obtained by electrospinning a tungsten oxide precursor/PVP composite spinning solution containing a NaCl salt and the apoferritin template containing the Pt nanoparticle catalyst synthesized by electrospinning.

Figure 6:
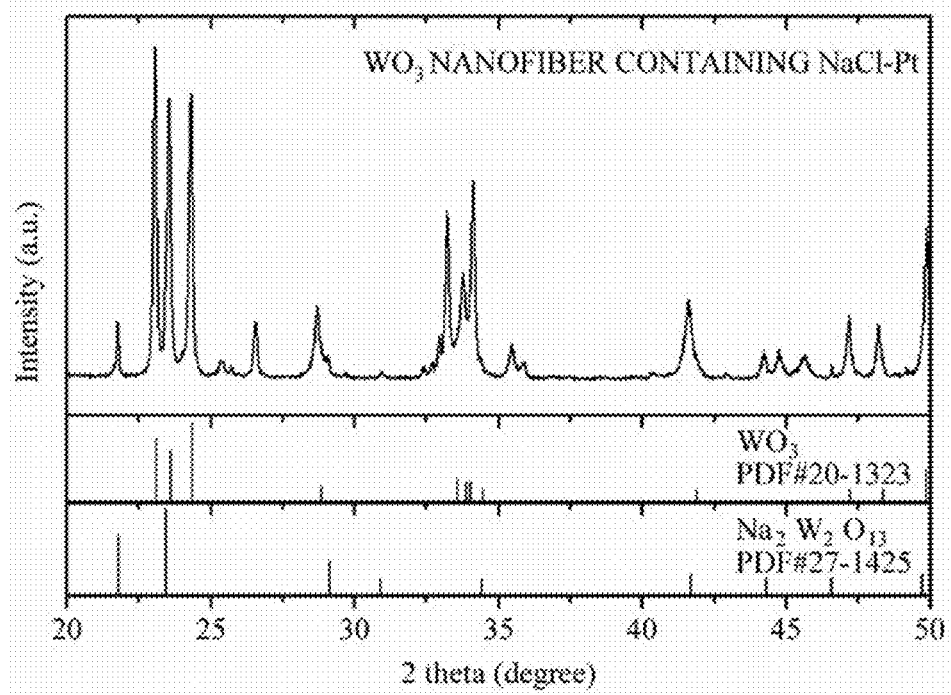
FIG. 6 is a graph of X-ray diffraction (XRD) analysis of one-dimensional tungsten oxide nanofibers doped with the Pt nanoparticle catalysts and Na according to Example 2.

FIG. 6 is a graph of X-ray diffraction (XRD) analysis of one-dimensional tungsten oxide nanofibers doped with the Pt nanoparticle catalysts and Na. Referring to FIGS. 5 and 6, it can be seen that, during the high-temperature heat treatment, a Na element of the NaCl salt reacted with the tungsten oxide precursor to form a $Na_2W_4O_{13}$ phase such that the Na element was functionalized to the tungsten oxide matrix.

Comparative Example 1: Manufacturing of Structure of Pure One-Dimensional $WO_3$ Nanofibers 100

Figure 7:
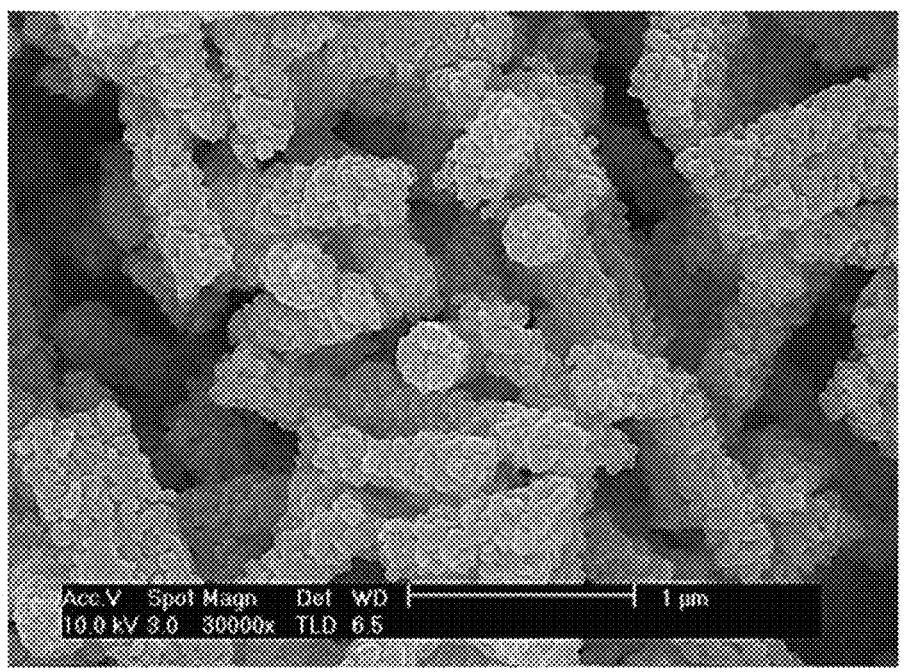
FIG. 7 is a SEM photograph showing one-dimensional pure tungsten oxide nanofibers which are synthesized according to Comparative Example 1.

Ammonium tungsten metatungstate hydrate, which is a tungsten oxide precursor, and 0.333 g of PVP polymer having a molecular weight of 1,300,000 g/mol were additionally dissolved in 2 g of deionized water and mixed. The mixed solution was stirred at 500 rpm at room temperature for twelve hours to prepare a spinning solution. The prepared spinning solution was put in a syringe (Henke-Sass Wolf, 12 mL NORM-JECT®), the syringe was connected to a syringe pump, the electrospinning solution was pushed out at a discharge rate of 0.1 ml/min, and then electrospinning was performed by applying a voltage of 15 kV between a needle (25 gauge), which was used during spinning, and a current collector that collect nanofibers. In this case, a stainless steel plate was used as the current collector, and a distance between the nozzle and the current collector was set to 20 cm. Thereafter, the polymer material was removed through an oxidation process, and the metal oxide precursor was oxidized to form tungsten oxide. In this case, a condition of the high-temperature heat treatment may be achieved by raising a temperature to 600° C. at a temperature increase rate of 5° C./min and then maintaining the temperature of 600° C. for one hour, and a temperature decrease rate may be kept constantly at 40° C./min. FIG. 7 is a SEM photograph showing one-dimensional pure tungsten oxide nanofibers which are synthesized according to Comparative Example 1.

Experimental Example 1: Manufacturing of Gas Sensor Using Nanofibers for Gas Sensor Prepared in Example 2 and Characteristic Evaluation In order to manufacture the gas sensor detection material prepared in Example 2 as a sensor for exhalation detection, 6 mg of a tin oxide nanofiber powder was distributed in 300 μl of ethanol and then pulverized using ultrasonic waves for five minutes. In this case, when the pulverization is performed for five minutes or more, nanofibers may be pulverized to have a very small length. The nanofiber detection material powder distributed in the ethanol may be applied on a top of a 3 mm×3 mm alumina substrate in which two parallel gold (Au) electrodes are formed and spaced a 150 μm interval from each other using a drop coating method. The coating process was performed such that 6 μl of nanomaterial solution pulverized and distributed in the ethanol, which was prepared in the above process, was applied on the alumina substrate with a sensor electrode part using a micropipette, and then the alumina substrate was dried on a hot plate heated at a temperature of 60° C. This process may be repeated two to five times to allow a sufficient amount of the detection material to be uniformly applied on the alumina sensor substrate.

Simulation gas detection characteristic evaluation as an exhalation sensor is performed using a sensor on which the detection material prepared through the above process is applied. The evaluation performs reactivity characteristic evaluation on biomarker gases of diseases at different concentrations and different sensor operating temperatures in an 85 to 95% relative humidity (RH) atmosphere having humidity similar to a gas discharged through exhalation of a human.

Figure 8A:
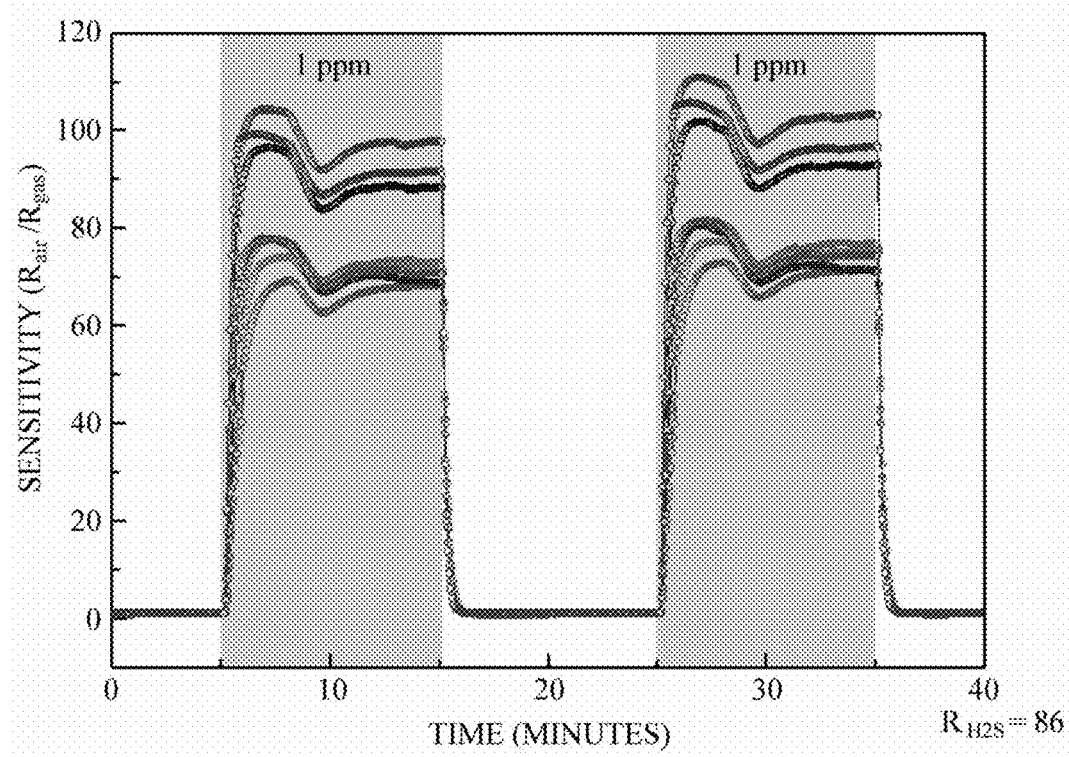
FIGS. 8A, 8B, and 8C are graphs showing sensitivity of a gas sensor manufactured according to an example embodiment with respect to hydrogen sulfide and ethanol.
Figure 8B:
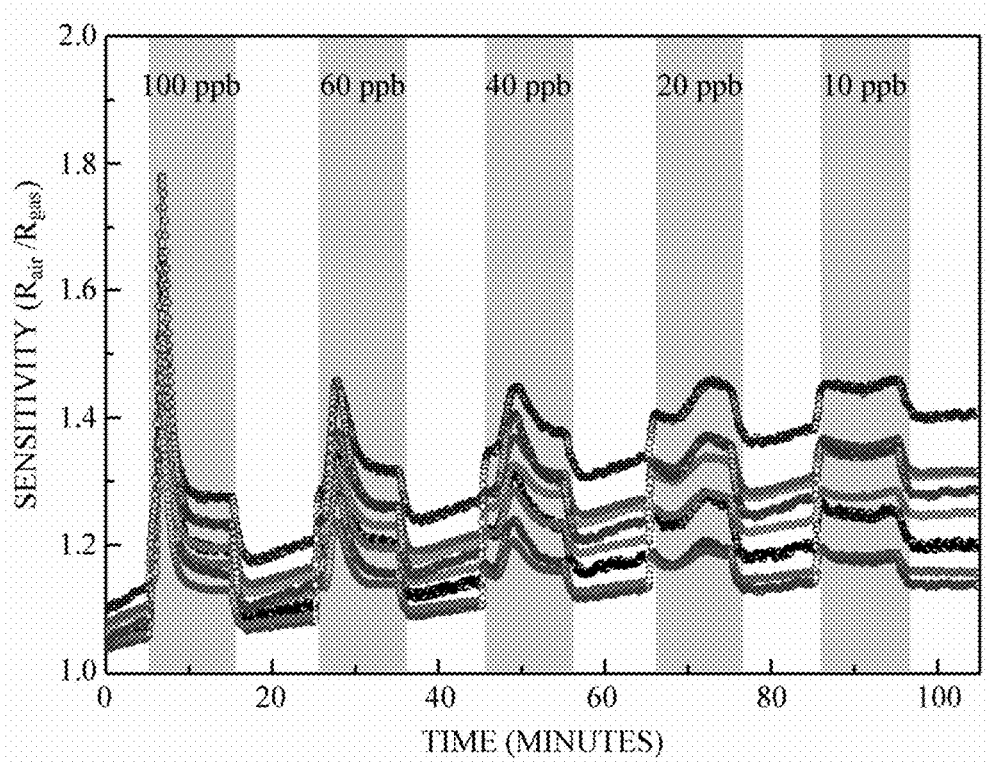
Figure 8C:
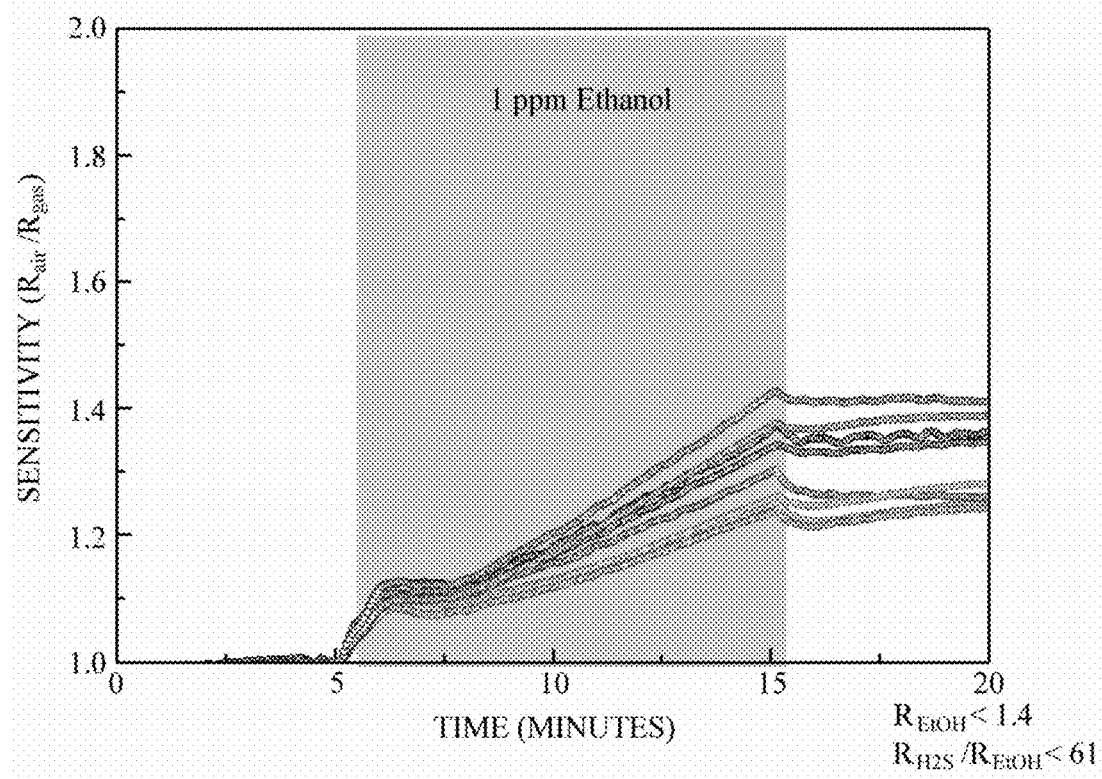

FIGS. 8A to 8C are graphs showing sensitivities of eight gas sensors manufactured according to an example embodiment with respect to hydrogen sulfide and ethanol. As can be seen from the illustrated graphs, the one-dimensional tungsten oxide nanofiber detection material doped with the Pt nanoparticle catalyst and Na exhibited a very high detection characteristic of an average sensitivity of 86 with respect to 1 ppm hydrogen sulfide gas and exhibited stable reactivity with respect to a trace amount of hydrogen sulfide at a level of 10 ppb. In addition, typically, it can be seen that the nanofiber detection material exhibited average sensitivity that is less than 1.4 with respect to the ethanol contained in exhalation and exhibited very high selectivity of 61 with respect to the hydrogen sulfide as compared with 1 ppm of ethanol which is a base.

FIGS. 9A and 9B are graphs showing stability of a gas sensor material and a gas sensor substrate which are manufactured according to an example embodiment. Referring to FIG. 9A, it can be seen that the one-dimensional tungsten oxide nanofiber detection material, in which the Pt nanoparticle catalyst and Na were compositely functionalized, and a gas sensor substrate, on which the detection material was applied, exhibited excellent stability with respect to eight samples even with exposure and recovery of 1 ppm hydrogen sulfide, which were repeated eleven times. In addition, referring to FIG. 9B, as a result of repeating the same measurement after three weeks using the same samples, it can be seen that stable reactivity with respect to 1 ppm hydrogen sulfide was maintained.

Figure 10:
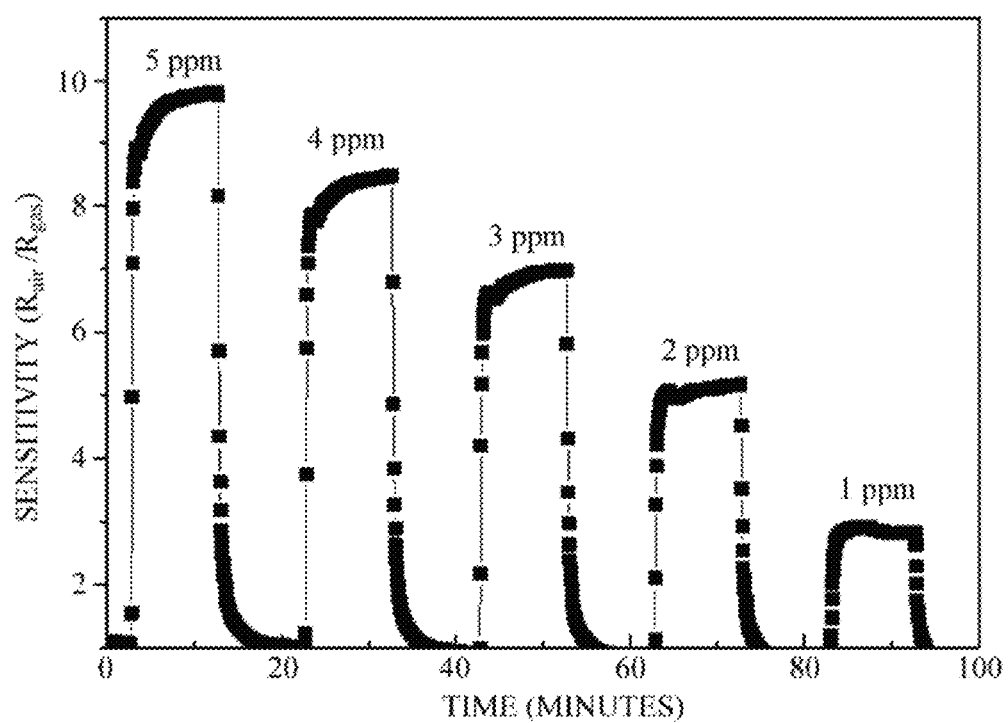
FIG. 10 is a graph showing a detection characteristic result of hydrogen sulfide using the pure tungsten oxide nanofibers which are synthesized in Comparative Example 1.

FIG. 10 is a graph showing a detection characteristic result of hydrogen sulfide using the pure tungsten oxide nanofibers which are synthesized in Comparative Example 1. When the nanofiber detection material was exposed to 5 to 1 ppm of hydrogen sulfide, it can be seen that a sensitivity value of about 10 was exhibited with respect to 5 ppm hydrogen sulfide and a sensitivity value of less than about 3 was exhibited with respect to 1 ppm hydrogen sulfide. Consequently, it can be seen that the nanofiber detection material exhibited low reactivity as compared with the detection material in which the composite catalyst of Pt and Na synthesized in Example 2 is functionalized.

Through Experimental Example 1, the sensor characteristic of the present gas sensor detection material with respect to the biomarker gases can be confirmed. In addition to the combination of the Pt nanoparticle catalyst and Na doping which exhibited the excellent detection characteristic with respect to hydrogen sulfide in Experimental Example 1, when various catalyst particles such as Au, Pd, Ru, Co, and Ni are synthesized and used instead of Pt, or other alkali or alkaline earth metal is doped instead of Na to synthesize poly metal oxide nanofibers in which poly catalyst particles are functionalized, nanosensor arrays with ultra-high sensitivity and ultra-high selectivity with respect to acetone ($CH_3COCH_3$) and toluene ($C_6H_5CH_3$), which are other biomarker gases, or $CO_2$, $NO_x$, $SO_x$, and $H_2$, which are harmful environmental gases, may be manufactured. The one-dimensional metal oxide nanofiber detection material, in which the nanoparticle catalyst synthesized with the apoferritin template is bound and which is doped with the alkali or alkaline earth metal, may have a positive effect of contributing to the development of the healthcare industry as an excellent gas sensor with respect to volatile organic compound/sulfur compounds contained in exhalation or with respect to a harmful environment.

Although the example embodiments are merely illustrative embodiments, it should be understood that numerous other alternations and modifications can be devised by those skilled in the art that will fall within the essential features of the present disclosure. Accordingly, the example embodiments are not intended to limit the technical spirit of the present disclosure but are merely illustrative and are not limited to these example embodiments. The scope of the present disclosure according to the above embodiments should be construed by the appended claims, along with the full range of equivalents to which such claims are entitled.

What is claimed is:

1. A member for a gas sensor, the member comprising: metal oxide nanofibers,
   wherein the metal oxide nanofibers comprise a metal nanoparticle catalyst and an alkali or alkaline earth metal bound to be functionalized between metal oxide nanoparticles serving as a matrix, and
   the metal oxide nanofibers are obtained by an electrospinning process followed by a heat treatment process.

2. The member of claim 1, wherein a diameter of the metal oxide nanofibers is in a range of 50 nm to 10 μm, and a length of the metal oxide nanofibers is in a range of 1 μm to 100 μm.

3. The member of claim 1, wherein the metal oxide nanoparticles are selected from the group consisting of $WO_3$, $ZnO$, $SnO_2$, $TiO_2$, $In_2O_3$, $Zn_2SnO_4$, $MnO_2$, which are n-type semiconductors, or is selected from the group consisting of $CuO$, $Co_3O_4$, $Fe_2O_3$, $Fe_3O_4$, $PdO$, $LaCoO_3$, $NiO$, $NiCo_2O_4$, and $Ag_2O$, which are p-type semiconductors.

4. The member of claim 1, wherein the metal oxide nanofiber has an open pore structure in a size range of 50 nm to 100 μm between the metal oxide nanofibers which are networked and interconnected.

5. The member of claim 1, wherein the metal nanoparticle catalyst is manufactured from an apoferritin protein template having a hollow structure with an inside diameter ranging from 7 nm to 8 nm.

6. The member of claim 5, wherein the metal nanoparticle catalyst is synthesized by injecting a metal salt into the apoferritin protein template and performing reduction treatment through a reducing agent.

7. The member of claim 6, wherein the metal salt contains one or more selected from the group consisting of Pt, Pd, Rh, Ru, Ni, Co, Cr, Ir, Au, Ag, Zn, Mn, Ga, Ge, W, Sn, Sr, In, Pb, Ta, Sb, Sc, and Ti.

8. The member of claim 1, wherein a size of the metal nanoparticle catalyst is in a range of 1 nm to 5 nm.

9. The member of claim 1, wherein the alkali or alkaline earth metal includes one or more selected from the group consisting of Na, K, Mg, Ca, Rb, Sr, Cs, and Ba.

10. The member of claim 1, wherein the metal oxide nanofiber includes a second phase which is formed due to a reaction of the alkali or alkaline earth metal with the metal oxide nanofiber matrix through the heat treatment process.

11. The member of claim 1, wherein the metal oxide nanofiber includes a plurality of heterointerfaces formed so that a second phase is formed due to reaction of the alkali or alkaline earth metal with the metal oxide nanofiber matrix and formed between the metal oxide nanofiber matrix, the second phase, and the metal nanoparticle catalyst.

12. The member of claim 11, wherein the alkali or alkaline earth metal includes Na, and the metal oxide nanofiber matrix includes $WO_3$.

13. A method of manufacturing metal oxide nanofibers, the method comprising:
   synthesizing a nanoparticle catalyst inside an apoferritin protein template;
   preparing a spinning solution by stirring the apoferritin template containing the nanoparticle catalyst and an alkali or alkaline earth metal salt with a metal oxide precursor/polymer composite solution;
   electrospinning the spinning solution to synthesize metal oxide precursor/polymer composite nanofibers in which the nanoparticle catalyst and the alkali metal or alkaline earth metal salt are uniformly distributed; and
   synthesizing one-dimensional porous metal oxide nanofibers by performing heat treatment on the synthesized composite nanofibers.

14. The method of claim 13, wherein, in the synthesizing of the nanoparticle catalyst, a metal salt is injected into inner pores of the apoferritin protein template, and a reduction treatment is performed using a reducing agent to synthesize the metal nanoparticle catalyst.

15. The method of claim 13, wherein, in the preparing of the spinning solution, a weight ratio of the polymer to the nanoparticle catalyst is in a range of 1:0.00001 to 1:0.1.

16. The method of claim 13, wherein, in the preparing of the spinning solution, a weight ratio of the polymer to the alkali or alkaline earth metal salt is in a range of 1:0.00001 to 1:0.1.

17. The method of claim 13, wherein, in the preparing of the spinning solution, stirring is performed at a temperature ranging from 20 degrees Celsius to 40 degrees Celsius for four to twenty-four hours.

18. The method of claim 13, wherein, in the synthesizing of the metal oxide nanofibers, the nanoparticle catalyst and a second phase generated due to the alkali or alkaline earth metal salt are uniformly distributed and bound through the heat treatment.

19. The method of claim 13, wherein, in the synthesizing of the metal oxide nanofibers, the heat treatment is performed at a temperature ranging from 500 degrees Celsius to 800 degrees Celsius.

20. The method of claim 13, wherein, in the synthesizing of the metal oxide nanofibers, the apoferritin protein template and the polymer are thermally decomposed and removed through the heat treatment, and the metal oxide precursor is oxidized to form a one-dimensional metal oxide nanofiber structure.

* * * * *